(12) United States Patent
Atterbury et al.

(10) Patent No.: US 10,363,377 B2
(45) Date of Patent: Jul. 30, 2019

(54) NEEDLE SHIELD PULLER CAP ASSEMBLY

(71) Applicant: Eli Lilly and Company, Indianapolis, IN (US)

(72) Inventors: William G. Atterbury, Columbus, OH (US); Eric Gustin Hassenpflug, Westerville, OH (US); Steven Michael Madland, Columbus, OH (US); Christopher Paul McKenzie, Lancaster, OH (US); Mark Lafever, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 240 days.

(21) Appl. No.: 15/527,020

(22) PCT Filed: Dec. 1, 2015

(86) PCT No.: PCT/US2015/063176
§ 371 (c)(1),
(2) Date: May 16, 2017

(87) PCT Pub. No.: WO2016/089864
PCT Pub. Date: Jun. 9, 2016

(65) Prior Publication Data
US 2017/0354790 A1    Dec. 14, 2017

Related U.S. Application Data

(60) Provisional application No. 62/086,937, filed on Dec. 3, 2014.

(51) Int. Cl.
*A61M 5/32*    (2006.01)
*A61M 5/20*    (2006.01)
(Continued)

(52) U.S. Cl.
CPC ........ *A61M 5/3204* (2013.01); *A61M 5/2033* (2013.01); *A61M 5/326* (2013.01);
(Continued)

(58) Field of Classification Search
CPC .................. A61M 5/3202; A61M 5/3204
(Continued)

(56) References Cited

U.S. PATENT DOCUMENTS

| 4,742,910 A | 5/1988 | Staebler |
| 4,900,309 A | 2/1990 | Netherton et al. |

(Continued)

FOREIGN PATENT DOCUMENTS

| JP | 2003220142 | 8/2003 |
| WO | 9507885 | 3/1995 |

(Continued)

OTHER PUBLICATIONS

Authority pertaining to International Application No. PCT/US2015/063176; Date of Mailing: Mar. 21, 2016.

*Primary Examiner* — Nathan R Price
*Assistant Examiner* — John A Doubrava
(74) *Attorney, Agent, or Firm* — M. Daniel Spillman (57) ABSTRACT

A puller assembly for removing a shield from around a needle of a syringe. The puller assembly includes a grip component and a cap. The grip component has a tubular body defining an interior hollow which axially receives the shield. The tubular body has a slit that allows it to be forcibly shifted from a first arrangement to a second arrangement to change the size of the interior hollow. The tubular body includes a radial inner face with at least one radial inward projection for directly engaging the shield. The cap is grippable by a user. The grip component is held by the cap when inserted within a cavity of the cap during manufacturing installation, and when so held at least one radial (Continued)

inward projection of the grip component engages the shield for removal of the shield from around the needle when the cap is moved. A method of mounting a puller assembly to a shield around a needle is also disclosed.

14 Claims, 13 Drawing Sheets (51) Int. Cl.
 *A61M 5/315* (2006.01)
 *A61M 5/31* (2006.01)
(52) U.S. Cl.
 CPC ......... *A61M 5/3213* (2013.01); *A61M 5/3158* (2013.01); *A61M 2005/206* (2013.01); *A61M 2005/2073* (2013.01); *A61M 2005/3143* (2013.01)
(58) Field of Classification Search
 USPC ........................................................ 604/500
 See application file for complete search history.

(56) References Cited

U.S. PATENT DOCUMENTS

| | | | |
|---|---|---|---|
| 4,929,232 A | 5/1990 | Sweeney et al. | |
| 5,147,325 A | 9/1992 | Mitchell et al. | |
| 5,858,008 A | 1/1999 | Capaccio | |
| 6,585,702 B1 | 7/2003 | Brunel | |
| 7,094,224 B2 | 8/2006 | Lourenco et al. | |
| 7,976,499 B2 | 7/2011 | Grunhut et al. | |
| 8,231,585 B2 | 7/2012 | Heinz et al. | |
| 8,568,365 B2 | 10/2013 | Reid | |
| 8,591,463 B1 | 11/2013 | Cowe | |
| 8,617,120 B2 | 12/2013 | Rowe et al. | |
| 2008/0228147 A1 | 8/2008 | David-Hegerich et al. | |
| 2008/0269692 A1 | 10/2008 | James et al. | |
| 2009/0054849 A1 | 2/2009 | Burnell et al. | |
| 2009/0120896 A1 | 5/2009 | Scarlata | |
| 2010/0286619 A1* | 11/2010 | Abry | A61M 5/2033 604/192 |
| 2012/0238961 A1 | 9/2012 | Julian et al. | |
| 2012/0323177 A1 | 12/2012 | Adams et al. | |
| 2014/0358083 A1* | 12/2014 | McLoughlin | A61M 5/20 604/154 |
| 2015/0112259 A1 | 4/2015 | Holmqvist et al. | |

FOREIGN PATENT DOCUMENTS

| | | |
|---|---|---|
| WO | 2007047200 | 4/2007 |
| WO | 2009081130 | 7/2009 |
| WO | 2011101379 | 8/2011 |
| WO | 2012000835 | 1/2012 |
| WO | 2012076386 | 6/2012 |
| WO | 2012085585 | 6/2012 |

* cited by examiner

NEEDLE SHIELD PULLER CAP ASSEMBLY

BACKGROUND OF THE INVENTION

The present invention pertains to pharmaceutical injection devices, and, in particular, to an assembly for removing a shield that protects a needle of a syringe.

Many automatic injector devices include a cap feature which when removed from the device removes a protective shield from a needle of the syringe of the device. The protective shield may consist of a multipart construction including an inner shield and an outer shield which are operatively connected together. The inner shield is relatively flexible or elastomeric and provides a sterile barrier around the needle and forms a seal with, for example, the syringe hub from which the needle extends. The inner shield also may seal the tip of the needle such as in designs where the needle is already in fluid communication with the syringe contents. The outer shield is made of a relatively rigid material and protectively surrounds and engages the inner shield. A pulling of the outer or rigid needle shield from the syringe pulls off the inner shield as well.

The cap feature of the device grips the rigid needle shield and serves to make easier the removal of the shield. The cap feature may be larger in diameter than the protective shield, or provided with a mechanical advantage to aid its removal, so as to be more readily grasped and removed by certain users than if the protective shield was removed alone. When the cap feature is removed from the device, which removal removes the protective shield as well due to the cap gripping the rigid needle shield, the needle is uncovered, although frequently still housed within the device prior to being extended therefrom during use, and ready for an injection.

One known cap feature that grips a rigid needle shield utilizes a two-piece assembly. The first piece includes a plastic cup with a tubular portion designed to fit over a rigid needle shield portion of a protective shield previously mounted to an injection needle. The second piece includes a larger diameter, rigid plastic base cap having a softer, grippable periphery that may be provided via a comolding or two shot molding process. Two openings formed through sides of the tubular portion of the plastic cup define a pair of diametrically opposed grip fingers that are resilient so as to be deflectable. Each finger has an inner surface with serrated ribs, and an outer surface with a ramp formed thereon. After the plastic cup is placed onto the rigid needle shield such that the serrated ribs of the resilient fingers are in angular alignment with detents on the rigid needle shield with which they cooperate, the base cap is mounted to the plastic cup so that the tubular portion of the cup inserts into a cavity of the base cap. During this insertion, the base cap interior surface that defines its cavity engages the ramps of the grip fingers to deflect the fingers inward such that the serrated ribs come into gripping contact with the rigid needle shield. The base cap is so mounted until its radial protruding tabs within the base of the cavity snap fit into an annular recess on the exterior of the cup tubular portion, thereby locking the base cap and the plastic cup together to allow them to function as a unit.

While known cap assemblies for removing rigid needle shields may provide a benefit to users, they are not without their shortcomings. For example, cap assemblies may be complex to make, or not be well suited for gripping only small portions of needle shields that are exposed. Cap assemblies may require forces to install that are unacceptably high, or may, in their mounting during manufacture, bend the needle or shift the protective shield already installed on the needle an unacceptable amount that adversely affects sealing of the needle.

Thus, it would be desirable to provide a puller assembly that can overcome one or more of these and other shortcomings of the prior art.

BRIEF SUMMARY OF THE INVENTION

In one form thereof, the present invention provides a puller assembly mountable to a shield around a needle of a syringe, the shield projecting in an axial direction through an opening in a housing of a device holding the syringe. The puller assembly includes a grip component having a tubular body defining an interior hollow which axially receives the shield. The tubular body includes opposite angular ends defining a slit that allows the tubular body to be forcibly shifted from a first arrangement to a second arrangement, wherein the interior hollow has different sizes in the first and second arrangements. The tubular body includes a radial inner face with at least one radial inward projection for directly engaging the shield. The tubular body includes first and second axial ends, wherein the first axial end is adapted to abut the housing with the second axial end not in contact with the shield during manufacturing installation. The puller assembly also includes a cap grippable by a user and including a body having a surface defining a cavity. The grip component is held by the cap when inserted within the cavity during manufacturing installation. At least one radial inward projection of the grip component, when the grip component is held within the cavity with the shield disposed in the interior hollow, engages the shield for removal of the shield from around the needle when the cap is moved from the housing.

In another form thereof, the present invention provides a method of mounting a puller assembly to a shield around a needle, the shield projecting in an axial direction through an opening in a housing. The method includes the steps of: providing a grip component having a tubular body defining an interior hollow, the tubular body including opposite angular ends defining a slit, the tubular body including a radial inner face with at least one radial inward projection for directly engaging the shield: placing the tubular body around the shield with the tubular body in an radially expanded arrangement in which the slit is larger than when the tubular body is in a neutral arrangement, wherein the shield extends within the interior hollow; allowing a resiliency of the tubular body to cause the tubular body to automatically return toward the neutral arrangement around the shield; and placing a grippable cap onto the grip component such that the tubular body fits within a cavity of the grippable cap so that the grippable cap backs up the grip component, whereby the at least one radial inward projection can engage the shield for removal purposes when the cap is moved from the housing.

One advantage of the present invention is that a puller assembly may be provided which can function within a range of axial tolerances at which the needle shield can be presented for gripping.

Another advantage of the present invention is that a puller assembly may be provided which can be mounted to a needle shield without requiring unacceptably large forces be applied or without adversely affecting a seal around a needle.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Figure 1:
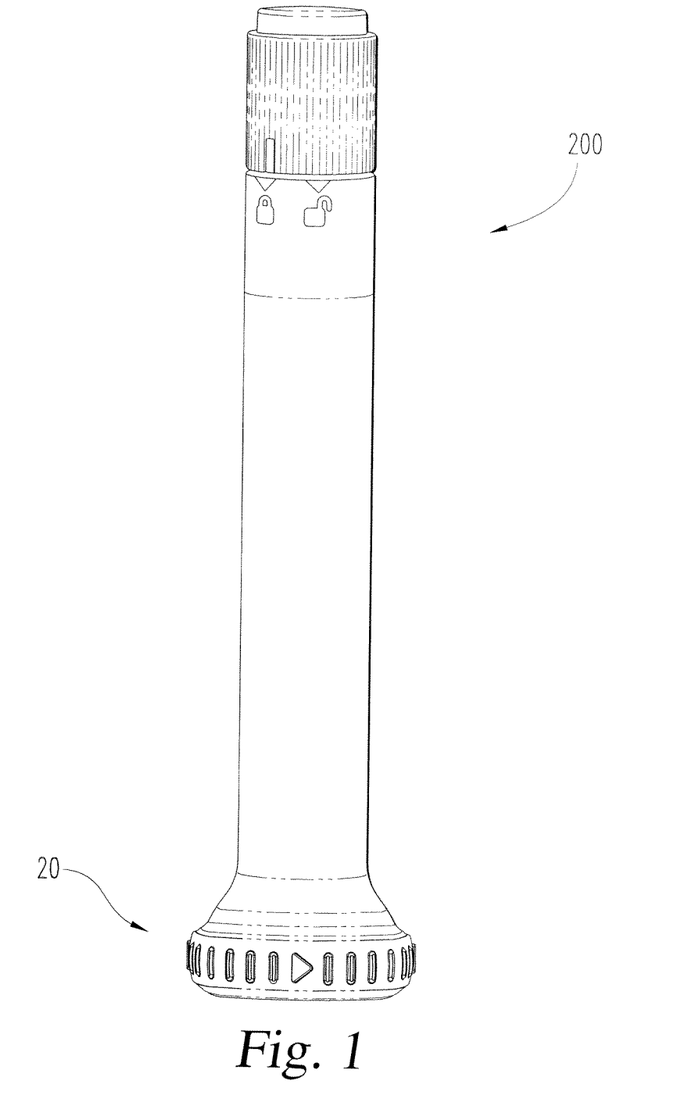
FIG. 1 is a front view of an automatic injection device equipped with a first embodiment of a needle shield puller assembly of the present invention.
Figure 2:
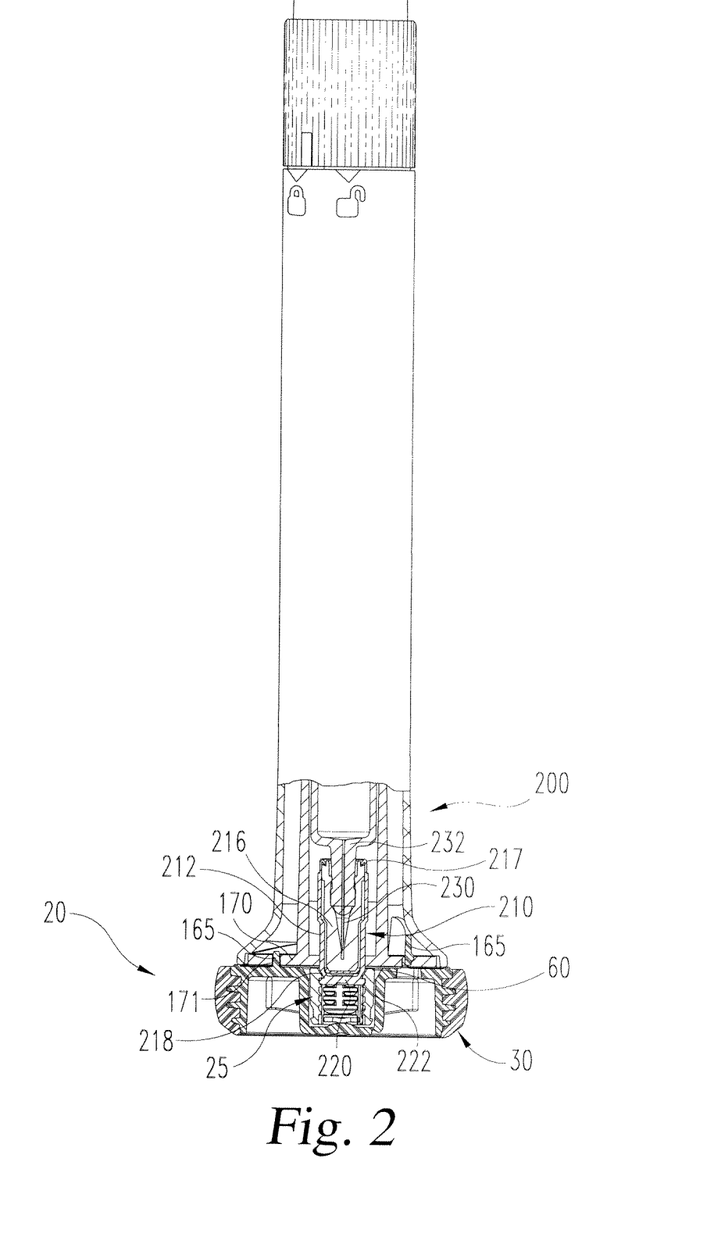
FIG. 2 is a view of the device of FIG. 1 in partial longitudinal cross-section further revealing the puller assembly.

In FIGS. 1 and 2, a first embodiment of a puller assembly of the present invention, generally designated 20, is shown mounted to an automatic injection device, generally designated 200. The puller assembly 20 is formed of an inner part or grip component, generally designated 25, and an outer part or cap, generally designated 30. Puller assembly 20 serves as a means for gripping a needle shield to allow a user to conveniently remove a needle shield that protectively surrounds a needle 230 of a syringe of device 200 in order to prepare that device for use. Device 200 does not form a part of the present invention, but may be, for example, an automatic injection device as disclosed in International Publication Number WO 2014/062488, the entire disclosure of which is incorporated herein by reference. The puller assembly 20 also may be used with injection devices that are not automatic.

Figure 8:
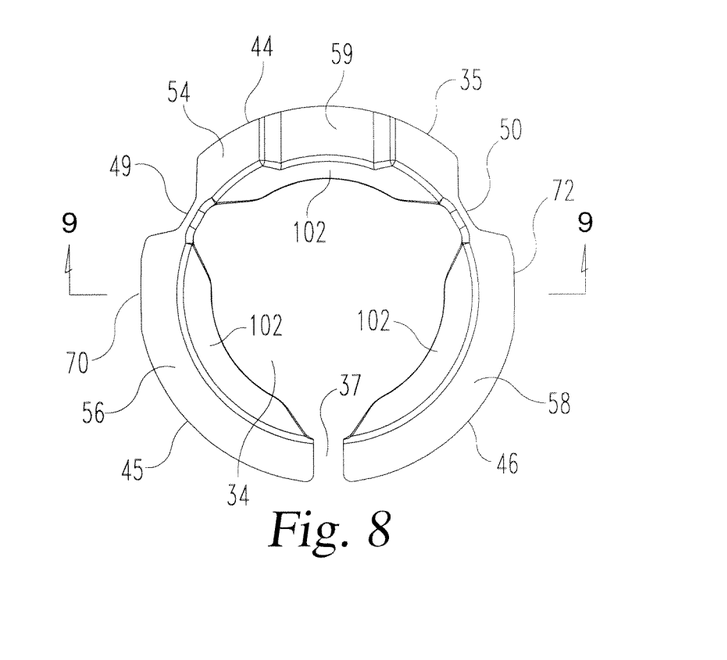
FIG. 8 is a top view of the grip component of FIG. 3.
Figure 9:
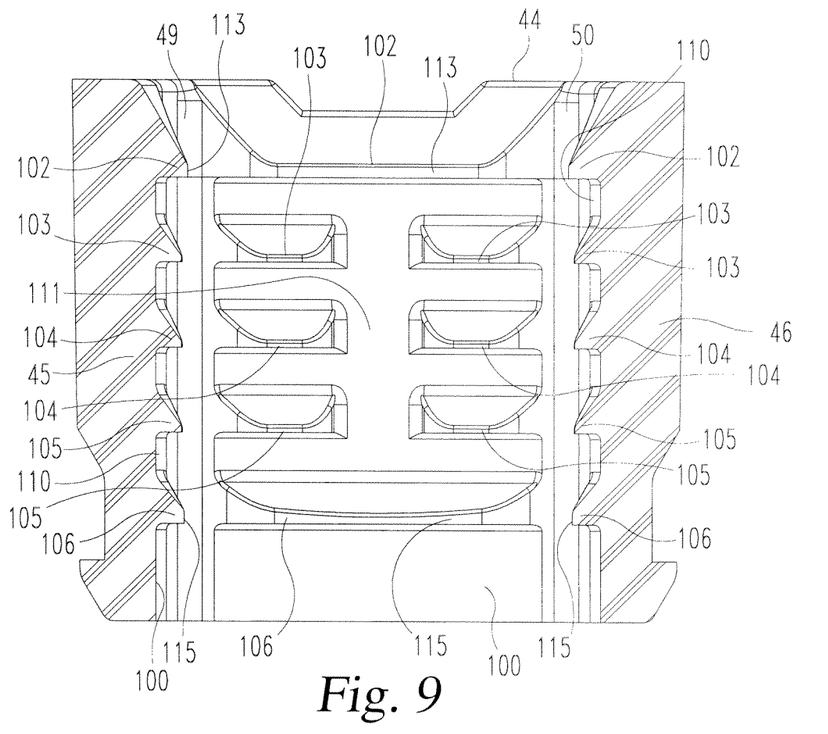
FIG. 9 is a longitudinal cross-sectional view of the grip component taken along line 9-9 of FIG. 8.
Figure 10:
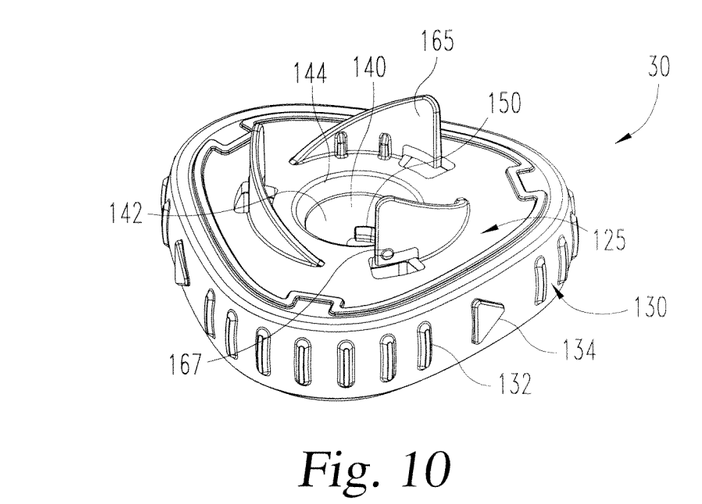
FIG. 10 is a top perspective view of only a cap of the puller assembly of FIG. 2.
Figure 11:
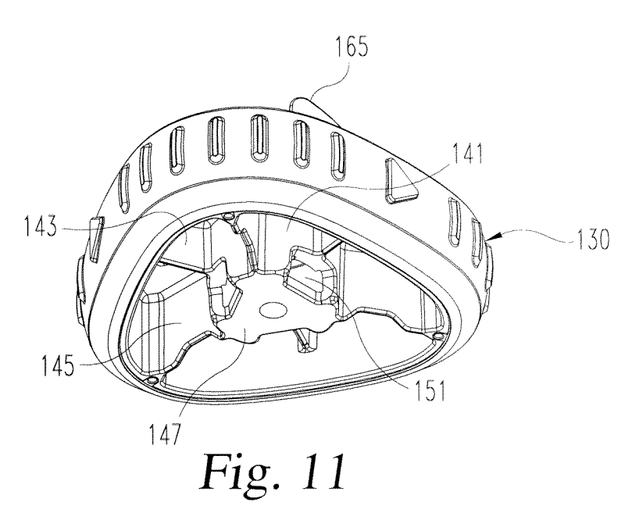
FIG. 11 is a bottom perspective view of the cap of FIG. 10.
Figure 12:
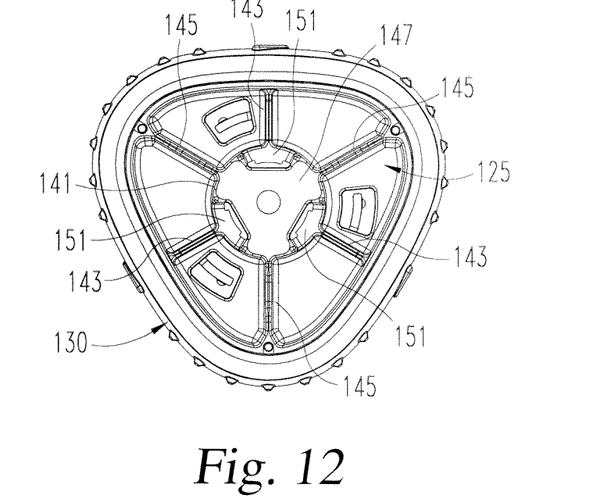
FIG. 12 is a bottom view of the cap of FIG. 10.
Figure 13:
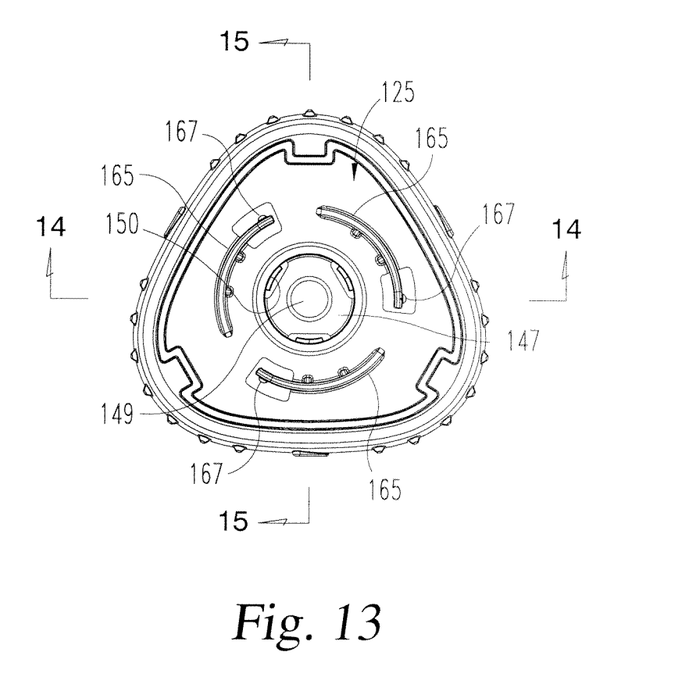
FIG. 13 is a top view of the cap of FIG. 10.
Figure 14:
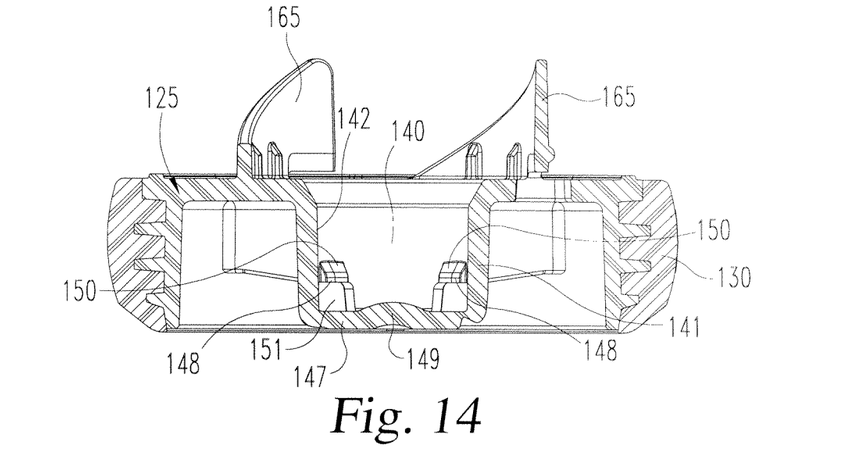
FIG. 14 is a longitudinal cross-sectional view of the cap taken along line 14-14 of FIG. 13.
Figure 15:
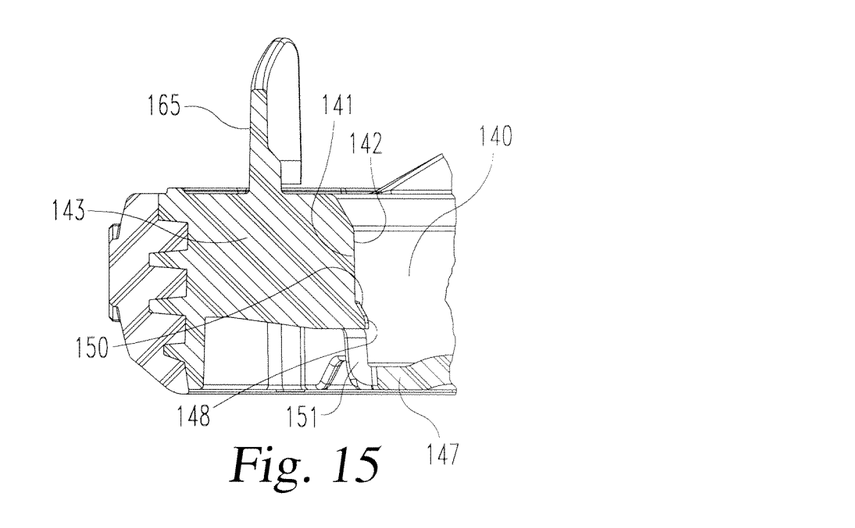
FIG. 15 is a partial view in longitudinal cross-section of the cap taken along line 15-15 of FIG. 13.

With additional reference to FIGS. 3-9, grip component 25 is shown in its neutral state separate from and prior to being used with cap 30 to grip a needle shield. Grip component 25 has a one-piece molded construction formed from a durable material such as polyoxymethylene. Grip component 25 has a tubular body 32 that defines an interior hollow 34. As shown in FIG. 8, tubular body 32 has a generally cylindrical outer periphery 35. This periphery may be differently shaped provided it and the cavity in cap 30 in which the body 32 fits are complementarily configured. For molding purposes, the outer periphery 35 tapers in diameter as is extends distally, or down in FIG. 3.

Figure 3:
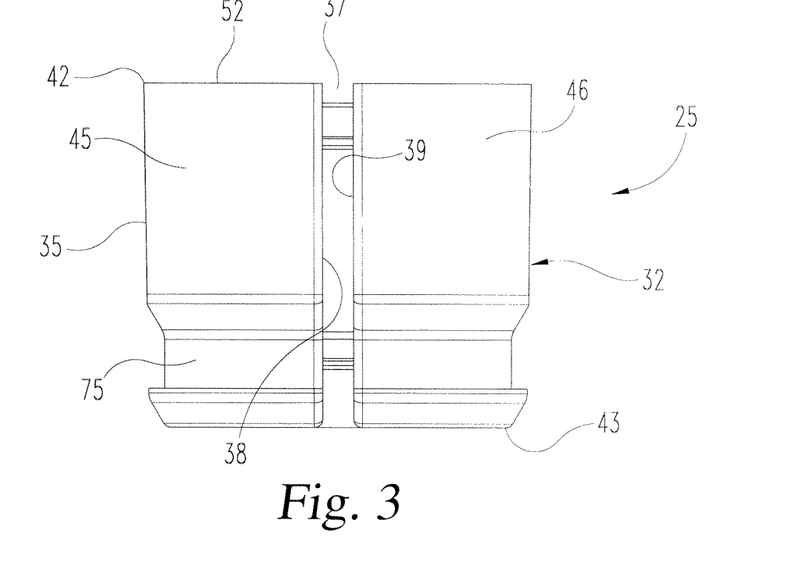
FIG. 3 is a front view of only a grip component of the puller assembly of FIG. 2 in its neutral state.
Figure 4:
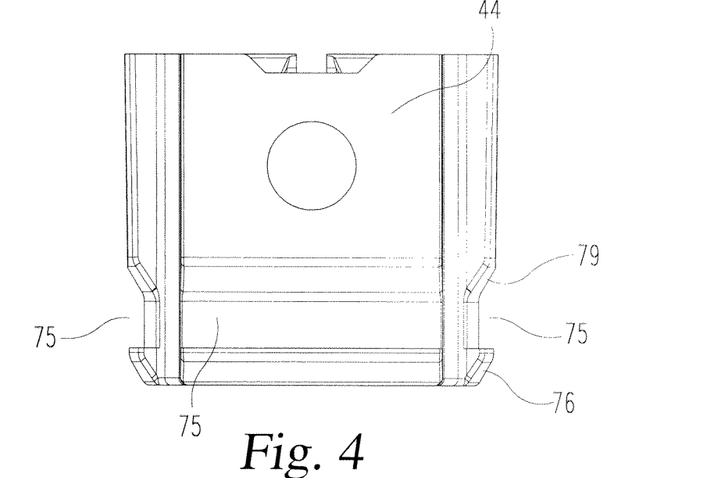
FIG. 4 is a rear view of the grip component of FIG. 3.
Figure 5:
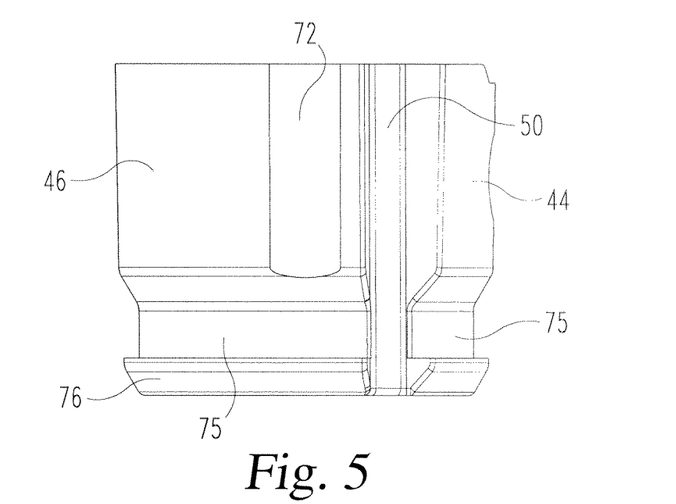
FIG. 5 is a right side view of the grip component of FIG. 3.
Figure 6:
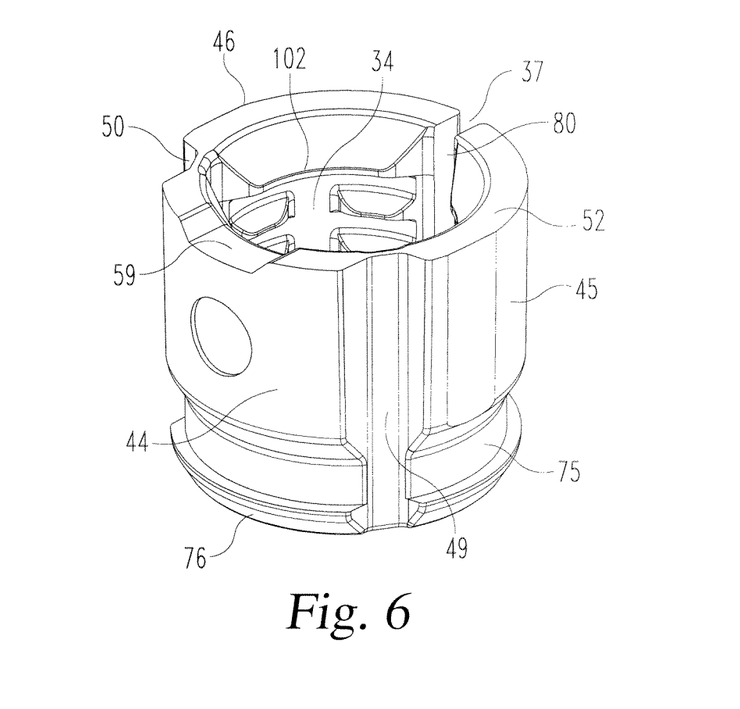
FIG. 6 is a top rear perspective view of the grip component of FIG. 3.
Figure 7:
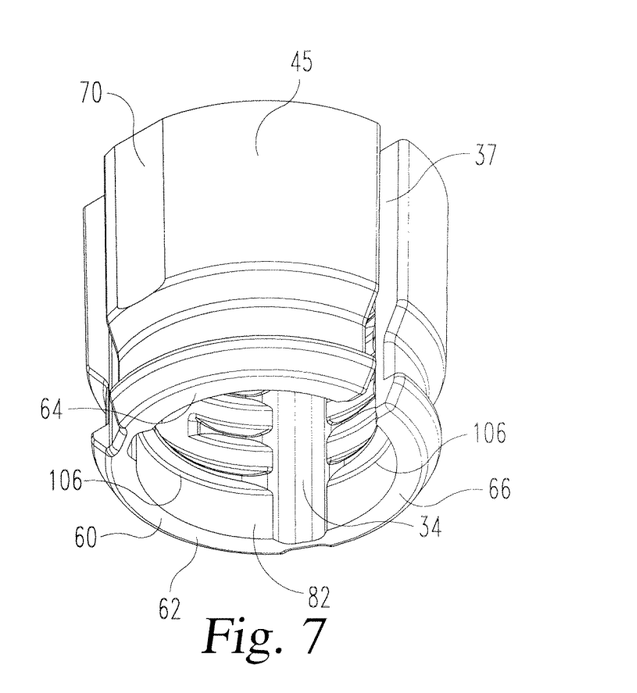
FIG. 7 is a bottom perspective view of the grip component of FIG. 3.

Body 32 is provided with a slit or split 37 that is defined by opposite angular ends 38 and 39 of body 32. Slit 37 allows body 32 to be manipulated to change the size of hollow 34 during installation. Slit 37 extends continuously from a first axial end 42 of body 32 to a second, opposite axial end 43. Slit 37 is shown as being straight and extending solely in the axial direction from end 42 to end 43. Other shapes, or anglings, of slit 37 may be used. Due to slit 37, body 32 generally has a C-shape configuration in a cross-section perpendicular to the axial direction.

Body 32 includes a plurality of rigid arcuate sections. Body 32 is shown including three arcuate sections 44, 45 and 46, but different numbers of sections may be employed. Body sections 45 and 46 are mirror images of each other. Hinge regions 49 and 50 of body 32 articulatably interconnect opposite angular ends of body section 44 with body sections 45 and 46. Hinge regions 49 and 50, formed to be thinner in radial thickness than the body sections 44-46, rigidly maintain the C-shape of the body absent external forces but provide points of bending or hinging on the body which facilitate the manufacturing process as well as operational installation of grip component 25.

Body 32 has an axially facing, generally flat surface 52 at end 42. Surface 52 is formed by the proximal faces 54, 56 and 58 of arcuate sections 44, 45 and 46 respectively, and notch 59 in surface 54 is for molding purposes. Surface 52 provides a bearing surface for the grip component 25 to engage a device housing through which the needle shield extends. Body 32 has an axially facing, generally flat surface 60 at end 43 formed by the distal faces 62, 64 and 66 of arcuate sections 44, 45 and 46 respectively.

As shown in FIG. 8, body sections 45 and 46 include flats 70, 72 in their otherwise curved outer periphery which in the circumferential direction are near to the hinged connections 49 and 50 with body section 44. Flats 70, 72 span a mold parting line to allow for flashing to not compromise the fit of grip component 25 with cap 30.

Each of body sections 44, 45 and 46 includes a groove 75 along its outer radial periphery, and a ramped distal edge 76 leading into groove 75. Groove 75 is angled at 79 to fit tang face 150 of cap 30.

Interior hollow 34 extends the entire axial length of body 32 from body axial end 42 to body axial end 43. Hollow 34 is shown having a generally cylindrical shape, but so long as a secure gripping is achieved, such shape may be different to account for the shape of the shield the grip component 25 is intended to engage. The opening 80 of body 32 into hollow 34 at end 42 which is ringed by surface 52 allows for axial insertion of the shield. Opening 82 of body 32 into hollow 34 is provided at end 43. In alternate embodiments, instead of body 32 being open at its distal end, and provided the flexibility provided by slit 37 and hinge regions 49 and 50 is not eliminated, the opening 82 could be reduced or eliminated, resulting in hollow 34 being partially or completely closed off, such that hollow 34 would be configured essentially as a blind bore. In such alternate embodiments, the body region that so closes off the hollow preferably is axially spaced from the rigid shield when held therein.

The interior periphery of body 32 is configured to engage the needle shield that fits within hollow 34. With primary reference to FIG. 9, interior face 100 of body section 44 includes a series of axially spaced, radial inward protrusions or teeth that extend in the circumferential direction. The interior surface, other than as affected by notch 59, and teeth that are provided on body section 44 are also present on body sections 45 and 46 and are identically referenced. Not all of the shown teeth are required, and as few as a single tooth may be used to engage the needle shield if configured to ensure a secure engagement.

The teeth on each of body sections 44-46 include a proximal row including a single tooth 102, a distal row including a single tooth 106, and three rows equally axially spaced therebetween including interrupted teeth 103, 104 and 105. The angular interruption 111 of teeth 103, 104 and 105 facilitates molding, as the mold core that is used to form the grip component has a land that forms interruption 111, which land projects radially and provides a surface along which the distal tooth 106 on each of body sections 44-46 rides along when the molded part 25 is axially moved in the proximal direction, namely in the direction that tooth 102 is relative to tooth 106, to be stripped from the mold.

Each tooth 102-106 includes an angled proximal face and a planar distal face oriented transverse to the axial direction. The anglings of the angled proximal faces, which as considered from their respective distal faces is the steepest for tooth 102, less steep and the same for teeth 103-105, and still less steep for tooth 106, generally correspond to the angling of needle shield taper 218. The anglings of the angled proximal faces also contribute to each tooth having an inward portion or tip of small axial profile to reduce the chance of any tooth tip engaging the radial periphery of disc portion 220 of a rigid shield 210 described further below. The angling also accommodates the disc portion 220 when such is engaged by the immediately proximal tooth. Suitable angles as measured from their respective distal faces are 60 degrees for tooth 102, 55 degrees for each of teeth 103-105, and 50 degrees for tooth 106. The least steep incline of the proximal face of tooth 106 is used to provide a thicker and more robust tooth inward portion. The hinge regions 49 and 50 are without teeth in the shown embodiment.

The axial spacing 110 between each row of teeth 102-106, and the angling of the proximal faces of the teeth, accommodates disc portion 220 of a rigid shield 210. The tooth geometry and axial spacing is designed to maximize the number of rows of teeth while providing sufficient tooth strength and space for disc portion 220 to fit therebetween. For a disc portion that is nominally one millimeter thick, a tooth pitch between the undersides of adjacent teeth 102-105 of about 1.4 millimeter, and a tooth pitch of about 1.5 millimeters between the undersides of teeth 105 and 106, is suitable. The provision of axially spaced teeth 102-106 allow grip component 25 to account for tolerances in device manufacture which may result in variability from device to device in how far the needle shield projects axially from the housing after assembly. For example, teeth 102 can engage a disc portion 220 of a needle shield that axially extends a minimum amount, in view of tolerances, from the device. Or, on the other extreme, teeth 106 can engage a needle shield disc portion 220 that axially extends a maximum amount within tolerances from the device.

Teeth 102 on body 32 project to tips 113 that are farther radially inwardly within hollow 34 than are the tips of teeth 103-106. Teeth 102 are also thicker in the axial direction at their tips 113 than the corresponding tip portions of teeth 103-105, to form a more robust or stronger inner edge. This farther projection, and more robust design, is to afford tips 113 the ability to act as a backup for needle shield engagement if during use the disc portion 220 slips past the inward tips of a different row of teeth which should have gripped the shield positioned thereunder previously. Teeth 106 on body 32 project radially inwardly from the body surfaces 100 farther than the teeth 103-105, and include tips 115 that in the axial direction are thicker than the tips of teeth 103-105, and are about the same thickness as the tips of teeth 102, to create robust teeth that can better withstand forces experienced during manufacture when the tips 115 slide along the mold core during part stripping. The portions of teeth 106 that are angularly aligned with interruptions 111 extend even further radially inward than the remainder of the teeth 106 to facilitate removal from a mold during manufacture.

The puller assembly cap 30 is further shown in FIGS. 10-15. Cap 30 is formed of a two shot molding having a central body portion 125 and a gripping periphery 130. Body portion 125 is formed of a rigid material such as polycarbonate. Periphery 130 is molded onto body portion 125 out of a softer material, such as a thermoplastic elastomer such as Versaflex™, and includes knurling 132 to make it easier to grip, and directional arrows 134 to show how it can be twisted for removal from the device.

Body portion 125 includes a cup portion 141 with a central cavity 140 defined by a generally cylindrical, inner surface region 142 with a chamfered lead-in surface 144. Sets of ribs 143 and 145 brace the cup portion 141. Surface region 142 is designed to fit closely around gripping component 25 when placed thereover, with a size and shape that radially backs up the body 32 to prevent it from expanding. When so backed up, slit 37 can not enlarge in a manner that would undesirably allow the needle shield to slip out from the grip component 25. The base of cup portion 141 is formed by a base flange 147. The base flange 147 has a central convexity 149 into the cavity 140 for molding purposes.

Three equally angularly spaced tangs 148 inwardly project within cavity 140 in spaced relationship with base flange 147 and above openings 151. Ramped proximal faces 150 of tangs 148 aid in tangs 148 inserting into groove 75 during the connection of cap 30 to grip component 25. The connection of cap 30 to grip component 25 can be differently achieved in alternate embodiments, such as a friction fit or with an adhesive.

Three cams 165 that are equally angularly spaced around cavity 140 and which are arcuate in shape project upwardly from body portion 125. Cams 165 fit within arcuate slots 171 provided in the base plate 170 of the device housing show in FIG. 2. A detent 167 provided on each of cams 165 engages base plate 170 to provide a releasable connection of body portion 125 to the base plate to aid in keeping puller assembly 20 on device 200 until its removal is desired. The camming engagement of cams 165 with base plate 170 when a user rotates puller assembly 20 relative to the rest of device 200 in the direction of arrows 134 shifts the puller assembly 20 away from the rest of the device, overcoming the connection of detents 167 with the base plate 170, to facilitate puller assembly removal. The removal of the puller assembly 20 from device 200 may also be done without rotation of the puller assembly but merely by the user pulling it axially.

Figure 16:
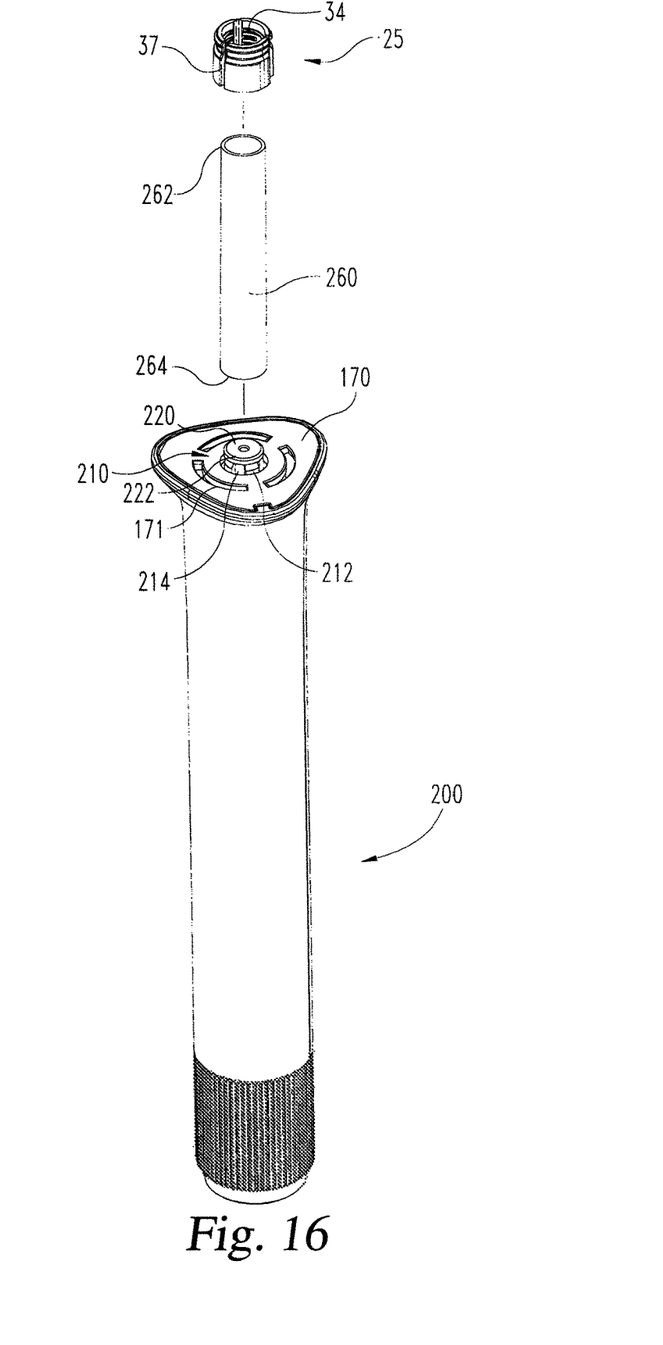
FIG. 16 is perspective view of a step in assembling a puller assembly to a rigid needle shield of an automatic injection device.

The structure of puller assembly 20 will be further understood in view of the following description of its assembly to a device by a manufacturer. In FIG. 16, injection device 200 is shown prepared for the attachment of a puller assembly 20 to the device's rigid needle shield 210 shown projecting beyond base plate 170. As puller assembly 25 can engage needle shields of various shapes so long as the one or more inner teeth of the puller assembly achieve a suitable gripping engagement, the shown configuration of the needle shield in the Figures is representative and not intended to be limiting.

Rigid needle shield 210, as further shown in FIG. 2, has a generally cylindrical region 212 with longitudinal slots 214 spaced around the circumference through which an elastomeric inner shield 216 is visible. The tip of projecting region 212 tapers at 218 and is integral with a disc portion 220 that is radially coextensive with projecting region 212. The leading outer edge 222 of disc portion 220 is rounded. Inner shield 216 seals the end of a needle 230 of a syringe 232 within device 200. Rigid needle shield 210 and inner shield 216 are interconnected at 217 so that the protective shield they provide together around the end of needle 230 is removable as a unit.

Assembly of the puller assembly 20 to rigid needle shield 210 begins with maneuvering a grip component 25, in its neutral state, into a position axially above a tapered mandrel or assembly tool 260 positioned above the rigid needle shield 210 as shown in FIG. 16. No specific rotational orientation of grip component 25 relative to device 200 is required. In this neutral state, grip component 25 has an arrangement in which the interior hollow 34 is sized the same as it will be when ultimately secured within cap 30 when assembly is complete.

Figure 17:
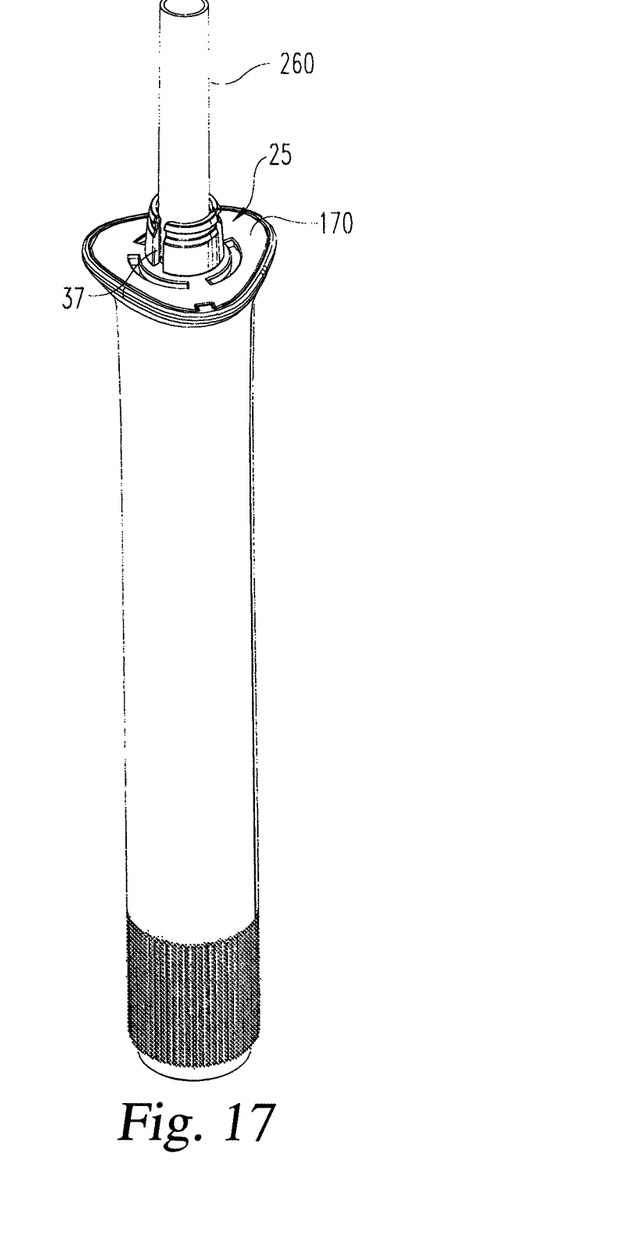
FIG. 17 is perspective view similar to FIG. 16 at a subsequent step of assembling.

Grip component 25 is then maneuvered such that tip 262 of mandrel 260 inserts through opening 80 into hollow 34, and the hollowed bottom tip 264 of mandrel 260 fits over needle shield 210. Grip component 25 is then forcibly slid down the length of the mandrel 260 until bearing surface 52 abuts housing base plate 170. Because mandrel 260 increases in outside diameter as it extends from tip 262 to tip 264, this sliding of grip component 25 causes the body 32 to splay open, increasing the size or angular span of slit 37 against the resiliency of the body construction, resulting in grip component 25 having an expanded arrangement shown in FIG. 17 in which the interior hollow 34 is sized larger than when in its neutral state. At this point the parts are arranged as shown in FIG. 17.

While grip component 25 is held against housing base plate 170, mandrel 260 is then axially pulled to be removed from around the needle shield 210. With the mandrel 260 removed, the natural resiliency of body 32 automatically returns grip component 25 toward its neutral state around the needle shield 210. If the distance that the needle shield disc portion 220 is spaced from base plate 170 happens to be such that disc portion 220 is axially disposed between the row of teeth 102 and row of teeth 103, grip component 25 will return completely to its neutral state with the row of teeth 102 having their angled proximal faces nesting within taper 218. Otherwise, the grip component 25 will not completely return to its neutral state, but rather will return only until the row of teeth 102 are pressed into a compressive contact with the radial periphery of needle shield 210 by the resilience of grip component 25.

Figure 18:
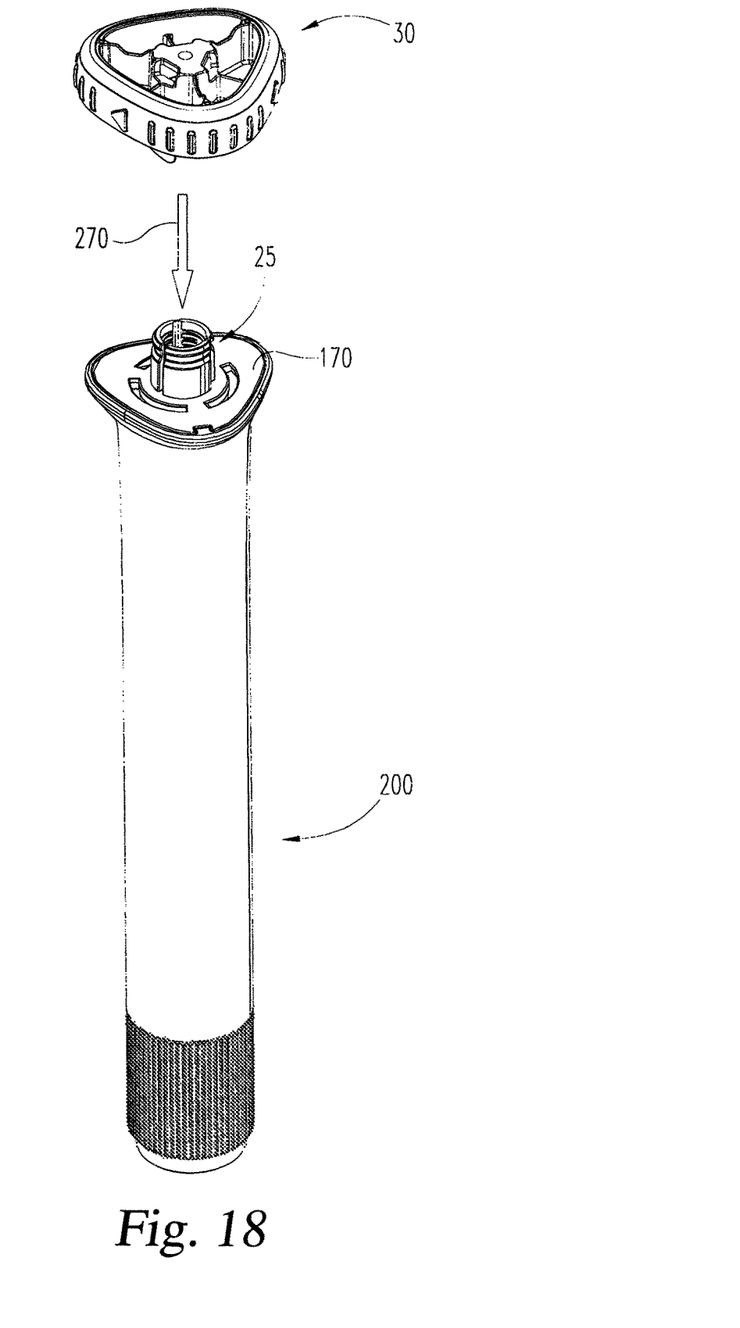
FIG. 18 is perspective view similar to FIG. 17 at a still subsequent step.

After cap 30 is then brought into a position axially above the grip component 25 generally surrounding the rigid needle shield 210, at which point the parts are arranged as shown in FIG. 18, the cap 30 is then moved down, as shown at arrow 270, such that the grip component 25 inserts within cavity 140 of cap 30.

During this insertion, the cap 30 will force grip component 25 to return to its original shape, or nearly so if cavity 140 expands slightly. During this forced return of grip component 25, a deformation of the grip component and needle shield, and/or a small relative axial movement of the cap 30 and grip component 25, occur. Specifically, the portions of the teeth and rigid needle shield 210 already in contact with each other, or brought into contact with each other during the forced return, deform slightly to form an even tighter grip, with the rigid needle shield tending to deform more as such is made of a softer material. A small axial shift, encouraged by the angled proximal faces of the teeth, also may occur to cause the rigid needle shield disc portion 220 to fit between rows of teeth. This small axial shift does not significantly affect the needle seal, such as due to axial clearance between parts that allows the entire syringe 232 to move in the device 20, and compliance in the parts such as the inner needle shield allowing deformation.

Figure 19:
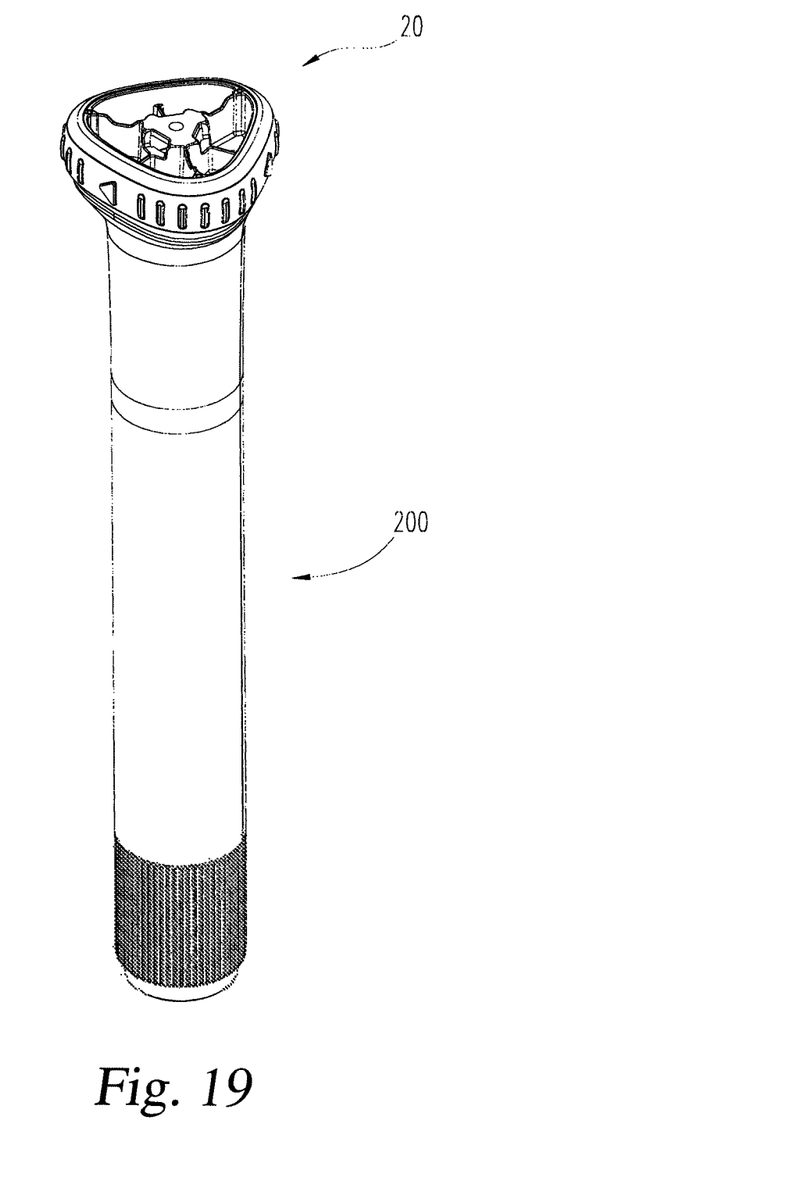
FIG. 19 is perspective view similar to FIG. 18 after the assembly is complete.

Insertion continues until halted when the cap tangs 148 snap fit into groove 75 of body sections 44-46, which snap fit ensures that cap 30 and grip component 25 are locked together to allow them to function as a unit for shield removal purposes. The snap fitting can occur due to elastic deformation of the cap 30, as aided by openings 151, and/or by the squeezing of the grip component 25 and the needle shield 210 therein. When the grip component 25 and cap 30 are so secured, which is shown in FIG. 19, cap 30 limits grip component 25 from expanding radially. When the device needle is to have its protective shield removed for use, the puller assembly 20 is simply removed from device 200, and due to one of the rows of teeth 102-106 engaging the disc portion 220, or by the teeth digging into the rigid needle shield, the gripped rigid needle shield 210 and the inner shield 216 that the rigid needle shield holds are removed simultaneously from over the needle 230.

While this invention has been shown and described as having preferred designs, the present invention may be modified within the spirit and scope of this disclosure. For example, while shown as being used to grip a rigid needle shield that contains an elastomeric inner shield, the puller assembly could directly engage an elastomeric shield if operational conditions allow. This application is therefore intended to cover any variations, uses or adaptations of the invention using its general principles. Further, this application is intended to cover such departures from the present disclosure as come within known or customary practice in the art to which this invention pertains.

We claim:

1. A puller assembly mountable to a shield around a needle of a syringe, the shield projecting in an axial direction through an opening in a housing of a device holding the syringe, the puller assembly comprising:
   a grip component having a tubular body defining an interior hollow which axially receives the shield, said tubular body including opposite angular ends defining a slit that allows said tubular body to be forcibly shifted from a first arrangement to a second arrangement, said interior hollow having different sizes in said first and second arrangements, said tubular body including a radial inner face with at least one radial inward projection for directly engaging the shield, said tubular body including first and second axial ends, said first axial end adapted to abut the housing with said second axial end not in contact with the shield during manufacturing installation; and
   a cap grippable by a user and including a body having a surface defining a cavity, said grip component held by said cap when inserted within said cavity during manufacturing installation, wherein said at least one radial inward projection of said grip component, when said grip component is held within said cavity with the shield disposed in said interior hollow, engages the shield for removal of the shield from around the needle when the cap is moved from the housing.

2. The puller assembly of claim 1 wherein said grip component comprises a one-piece construction.

3. The puller assembly of claim 2 wherein said grip component is made of a plurality of arc-shaped sections that are articulatably interconnected.

4. The puller assembly of claim 3 wherein said plurality of arc-shaped sections consists of three sections.

5. The puller assembly of claim 1 wherein said second axial end of said grip component body is open.

6. The puller assembly of claim 1 wherein said grip component body, in cross-section perpendicular to the axial direction, has a C-shape configuration.

7. The puller assembly of claim 1 wherein said at least one radial inward projection comprise a plurality of axially spaced teeth.

8. The puller assembly of claim 7 wherein a first tooth of said teeth which is closest to said second axial end extends farther radially inward than a second tooth that is closer to said first axial end.

9. The puller assembly of claim 8 wherein a third tooth of said teeth which is closest to said first axial end extends farther radially inward than said first tooth.

10. The puller assembly of claim 1 wherein said slit extends solely in the axial direction.

11. A method of mounting a puller assembly to a shield around a needle, the shield projecting in an axial direction through an opening in a housing, the method comprising:

providing a grip component having a tubular body defining an interior hollow, said tubular body including opposite angular ends defining a slit, said tubular body including a radial inner face with at least one radial inward projection for directly engaging the shield:

placing said tubular body around the shield with said tubular body in a radially expanded arrangement in which said slit is larger than when said tubular body is in a neutral arrangement, wherein the shield extends within said interior hollow;

allowing a resiliency of said tubular body to cause said tubular body to automatically return toward the neutral arrangement around the shield;

placing a grippable cap onto the grip component such that said tubular body fits within a cavity of said grippable cap so that the grippable cap backs up the grip component, whereby said at least one radial inward projection can engage the shield for removal purposes when the cap is moved from the housing.

12. The method of claim 11 wherein the step of placing said tubular body around the shield comprises sliding said tubular body from a first position to a second position along a mandrel that axially extends through the interior hollow and which has an end that first fits over the shield, the mandrel having a larger diameter at said second position than at said first position.

13. The method of claim 12 wherein when said tubular body is at said second position, a first axial end of said tubular body abuts the housing.

14. The method of claim 12 wherein the step of allowing a resiliency of said tubular body to cause said tubular body to automatically return toward the neutral arrangement around the shield comprises moving the mandrel out of the interior hollow.

\* \* \* \* \*